(12) United States Patent
Murphy et al.

(10) Patent No.: US 7,701,229 B2
(45) Date of Patent: Apr. 20, 2010

(54) METHODS AND SYSTEMS FOR MEASUREMENT OF FLUID ELECTRICAL STABILITY

(75) Inventors: Robert Murphy, Kingwood, TX (US); Dale Jamison, Humble, TX (US)

(73) Assignee: Halliburton Energy Services, Inc., Duncan, OK (US)

( * ) Notice: Subject to any disclaimer, the term of this patent is extended or adjusted under 35 U.S.C. 154(b) by 196 days.

(21) Appl. No.: 11/872,087

(22) Filed: Oct. 15, 2007

(65) Prior Publication Data

US 2009/0096440 A1  Apr. 16, 2009

(51) Int. Cl.
- G01R 27/08 (2006.01)
- G01R 27/22 (2006.01)
- G01V 3/00 (2006.01)

(52) U.S. Cl. .................. 324/698; 324/92; 324/366
(58) Field of Classification Search .......... 324/698
See application file for complete search history.

(56) References Cited

U.S. PATENT DOCUMENTS

| | | | |
|---|---|---|---|
| 2,859,404 A | 11/1958 | Crittendon | 324/30 |
| 4,524,325 A | 6/1985 | Moore et al. | |
| 6,906,535 B2 | 6/2005 | Murphy, Jr. et al. | 324/713 |
| 2003/0206024 A1 | 11/2003 | Murphy, Jr. et al. | |
| 2006/0016688 A1* | 1/2006 | Carrier et al. | 204/660 |
| 2007/0235336 A1* | 10/2007 | Carrier et al. | 204/571 |

FOREIGN PATENT DOCUMENTS

| | | |
|---|---|---|
| GB | 2 364 777 | 2/2002 |
| WO | WO 89/08838 | 9/1989 |
| WO | WO 00/45133 | 3/2000 |
| WO | WO 2005/040780 | 5/2005 |
| WO | WO 2007/055786 | 5/2007 |

OTHER PUBLICATIONS

Foreign communication related to a counterpart application dated Jan. 20, 2009.

* cited by examiner

*Primary Examiner*—Timothy J Dole
(74) *Attorney, Agent, or Firm*—John W. Wustenberg; Baker Botts, LLP

(57) ABSTRACT

The invention relates particularly to methods and apparatuses for characterizing water-in-oil or invert emulsion fluids for use in drilling well bores in hydro-carbon bearing subterranean formations. A fluid stability measurement device is disclosed. The device comprises a reference electrode and a second electrode coupled to an insulating body. A guard electrode is placed in the path between the reference electrode and the second electrode on the surface of the insulating body.

13 Claims, 4 Drawing Sheets

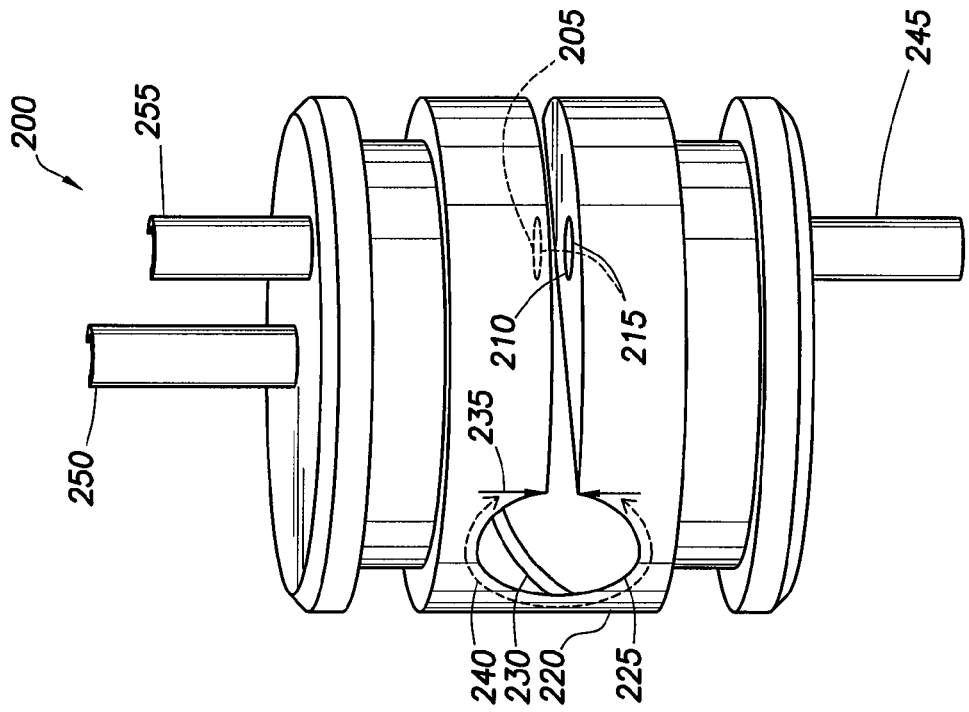
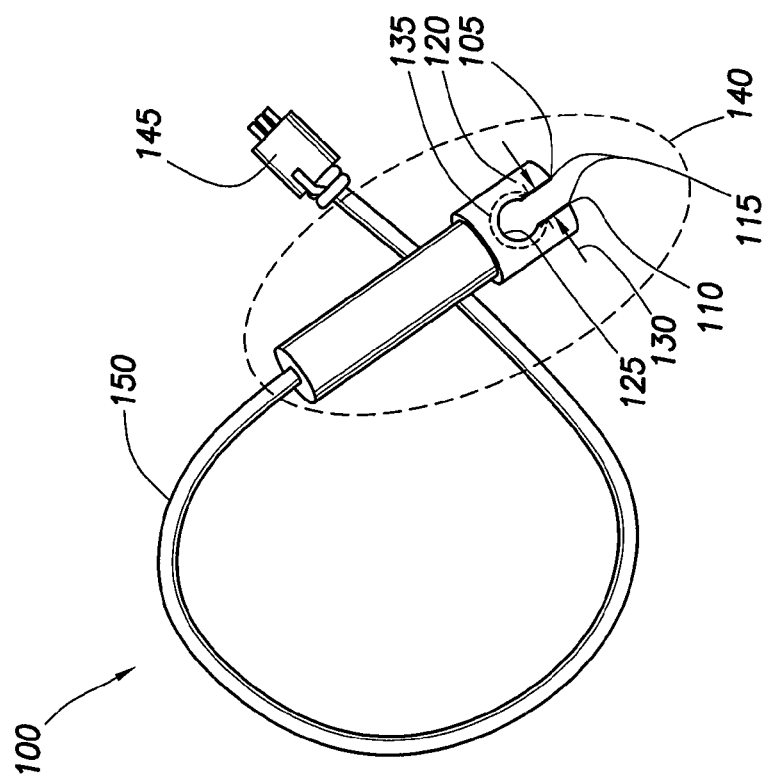
FIG.2
FIG.1
(PRIOR ART)

METHODS AND SYSTEMS FOR MEASUREMENT OF FLUID ELECTRICAL STABILITY

BACKGROUND OF THE INVENTION

The present invention relates to methods and apparatuses for characterizing or evaluating the strength or effectiveness of oil-based drilling fluids for use in drilling well bores in subterranean formations. The invention relates particularly to methods and apparatuses for characterizing water-in-oil or invert emulsion fluids for use in drilling well bores in hydrocarbon bearing subterranean formations.

Drilling fluids are frequently used in oil and gas drilling operations. These fluids serve many purposes including, but not limited to, removing the cuttings produced, lubricating and cooling the drill bit, and supporting the walls of the hole being drilled.

Oil-based drilling fluids are frequently used when drilling wells for oil and gas. These oil-based drilling fluids are typically water-in-oil emulsions that are stabilized with the addition of emulsifiers. The water phase is usually about 5% to about 40% of the total liquid volume and is usually comprised of (but not limited to) calcium chloride brine. If the formulation of the invert emulsion drilling fluid becomes unbalanced, due to, for example (without limitation), contamination, improper product additions, or thermal degradation, the oil-based drilling fluids tend to revert to an oil-in-water emulsion. As a result of the reversion to an oil-in-water emulsion, the water becomes the continuous phase and can cause the solids in the drilling fluid to become water wet. Such wetting has significant negative consequences to a drilling operation and requires expensive remedial action in order to prevent the loss of the well.

An Electrical Stability Tester (EST), such as the Fann 23D available from Fann Instrument Company in Houston, Tex., is typically used to characterize invert emulsion oil-based drilling fluids. The probe of the Fann 23D EST is shown generally in FIG. 1. The EST probe consists of a connector, a high voltage cable, and a molded electrode arrangement (probe). The EST probe is assembled with two electrodes precisely spaced apart in a molded, electrically insulating material such as plastic. In order to characterize the stability of an oil-based drilling fluid, the probe is placed into a sample of the oil-based drilling fluid such that the fluid fills the gap between the electrodes. The oil-based drilling fluids are typically water-in-oil emulsions with oil being the continuous phase. Therefore, the oil-based drilling fluid acts as an insulator. An increasing AC voltage is applied to the oil-based drilling fluid sample, across the two electrodes, while the current flow between them is monitored. Once the potential difference between the electrodes reaches a certain level, the oil-based drilling fluid will break down and a conductive path will be formed between the two electrodes. The peak voltage required to cause the breakdown is defined as Electrical Stability of the oil-based drilling fluid. The American Petroleum Institute's "Recommended Practice Standard Procedure for Field Testing Oil-Based Drilling Fluids", API Recommended Practice 13B-2, Third Edition, February 1998 ("the API Procedure"), is incorporated herein by reference. Paragraph 8.1.1 of the API Procedure defines the Electrical Stability of an oil-based drilling fluid as "the voltage in peak volts-measured when the current reaches 61 µA." Frequent measurements of Electrical Stability must be obtained in order to monitor the strength and characteristics of the oil-based drilling fluid during the drilling operations. Typically a Mud Engineer in the field must manually carry out the necessary steps to obtain an Electrical Stability measurement.

However, the typical method of use of an EST, as discussed above, has many drawbacks. One disadvantage of the current method is that the oil-based drilling fluid sample must be screened with a Marsh funnel and heated or cooled to the test temperature prior to each measurement in order to obtain consistent Electrical Stability values. This can be time consuming and burdensome. Another shortcoming of the current method is that the probe must be held stationary in the sample during the measurements in order to obtain repeatable measurements.

Yet another problem with the current method is that the contamination on the surface of the molded insulation of the EST probe can create a conductive path around the electrode gap allowing the current flow between the electrodes to bypass the sample in the gap. In order to reduce the impact of the contaminants, the probe must be very carefully cleaned between the measurement of different samples in order to prevent the build up of insulating or conducting films on the surface of the probes. Currently, this cleaning is accomplished using ultrasonic cleaning, solvents or passing rags or paper towels through the electrode gap in order to mechanically clean the probe.

The above pitfalls associated with the current method of measuring Electrical Stability make this method time consuming and prone to errors. The problem is further compounded by the fact that typically a Mud Engineer must manually obtain frequent Electrical Stability measurements during the drilling operations thereby making the current methods also labor intensive and expensive.

SUMMARY OF THE INVENTION

The present invention relates to methods and apparatuses for characterizing or evaluating the strength or effectiveness of oil-based drilling fluids for use in drilling well bores in subterranean formations. The invention relates particularly to methods and apparatuses for characterizing water-in-oil or invert emulsion fluids for use in drilling well bores in hydrocarbon bearing subterranean formations.

In one embodiment the present invention is directed to a fluid stability measurement device. The device comprises an insulating body, a reference electrode coupled to the insulating body having a first electrical potential, a second electrode coupled to the insulating body having a second electrical potential; and a guard electrode on a surface of the insulating body. A gap is formed between a surface of the reference electrode and a surface of the second electrode and the guard electrode is located in a surface path on the insulating body between the reference electrode and the second electrode.

In yet another embodiment, the present invention is directed to a method of determining electrical stability of a fluid comprising: placing the fluid in a gap between a reference electrode having a first potential and a second electrode having a second potential; coupling the reference electrode and the second electrode with an insulating material; intercepting a path on the insulating material between the reference electrode and the second electrode with a guard electrode; increasing a potential difference between the reference electrode and the second electrode; and measuring an amount of current flow between the reference electrode and the second electrode.

In one embodiment, the present invention is directed to an apparatus for measuring electrical stability of a fluid. The apparatus comprises a casing; a reference electrode having a first potential enclosed in the casing; and a second electrode having a second potential enclosed in the casing. An electrode gap is formed between a measurement surface of the reference electrode and a measurement surface of the second electrode. An insulating body is enclosed in the casing connecting the reference electrode and the second electrode; and a guard electrode is enclosed in the casing coupled to the insulating body. The guard electrode is positioned to intercept a path on the insulating body between the measurement surface of the reference electrode and the measurement surface of the second electrode.

The features and advantages of the present invention will be apparent to those skilled in the art. While numerous changes may be made by those skilled in the art, such changes are within the spirit of the invention.

BRIEF DESCRIPTION OF THE DRAWINGS

These drawings illustrate certain aspects of some of the embodiments of the present invention, and should not be used to limit or define the invention.

FIG. 1 is the probe of an Electrical Stability Tester in accordance with the prior art.

FIG. 2 is a side view of an improve Electrode Arrangement for an Electrical Stability Tester in accordance with an embodiment of the present invention.

DESCRIPTION OF PREFERRED EMBODIMENTS

Figure 3:
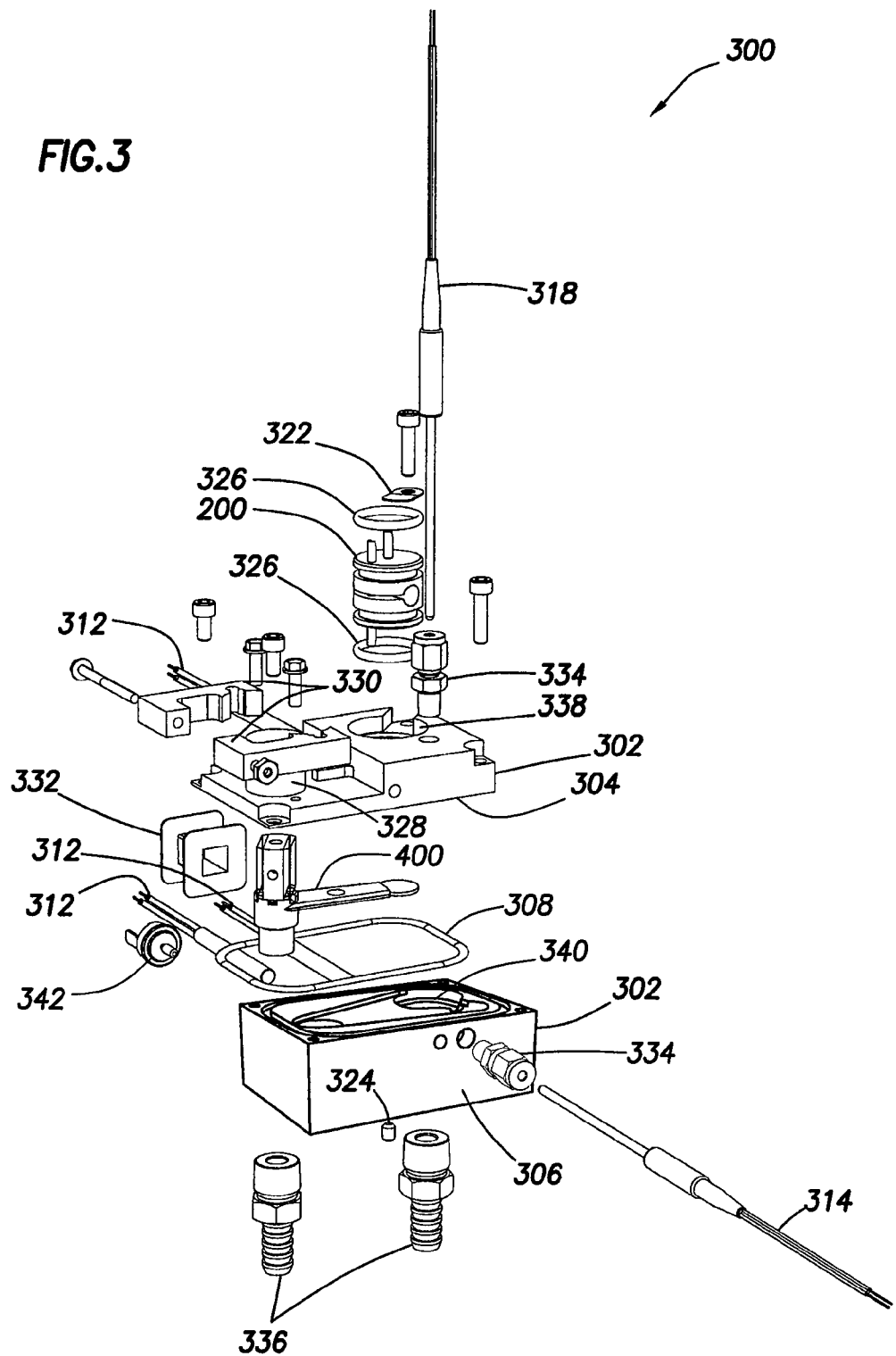
FIG. 3 is a blow up diagram of a Self Cleaning Electrical Stability Tester Cell in accordance with an embodiment of the present invention.

The present invention relates to methods and apparatuses for characterizing or evaluating the strength or effectiveness of oil-based drilling fluids for use in drilling well bores in subterranean formations. The invention relates particularly to methods and apparatuses for characterizing water-in-oil or invert emulsion fluids for use in drilling well bores in hydrocarbon bearing subterranean formations.

The details of the present invention will now be discussed with reference to the figures. Turning to FIG. 1, the Probe of an Electric Stability Tester (EST) in accordance with the prior art is shown generally by reference numeral 100. The Probe includes a First Electrode 105 and a Second Electrode 110 collectively referred to as the Measurement Electrodes 115. The Measurement Electrodes 115 are precisely spaced apart and molded into an Electrically Insulating Body 120. The Electrically Insulating Body 120 has a rounded Opening 125 at the end of the Electrode Gap 130 that extends the surface path between the Measurement Electrodes 115. This rounded Opening 125 reduces the effect of any conductive contaminant coating on the surface of the Insulating Body 120. Contamination on the surface of the Insulating Body 120 creates a Leakage Path 135 for the current flowing between the Measurement Electrodes 115. The Opening 125 extends the path between the Measurement Electrodes 115 thereby allowing less electrical current to flow between the Measurement Electrodes 115 through the surface of the Electrically Insulating Body 120 for a given electrical potential. The molded Electrode Arrangement 140 is coupled to a Connector 145 with a High Voltage Cable 150. In order to characterize the electrical stability of a fluid, the Electrode Arrangement 140 is placed such that the fluid fills the Electrode Gap 130. An increasing AC voltage is then applied across the Measurement Electrodes 115 while the current flowing between them is measured. Once the AC voltage is high enough the fluid will break down and a conductive path will be formed allowing for current flow between the Measurement Electrodes 115 through the fluid sample. The higher the peak voltage at which this break down occurs, the greater is the electrical stability of the fluid being tested. As would be appreciated by those of ordinary skill in the art, with the benefit of this disclosure, the potential difference across the Measurement Electrodes 115 which indicates the fluid's electrical stability may be measured using a potential measuring device, such as, for example, a volt meter.

However, as the Electrode Arrangement 140 is used in subsequent measurements, there will be a build up of conducting materials on the surface of the Electrically Insulating Body 120 which will act as a Leakage Path 135. Specifically, as conductive material builds up on the surface of the Electrically Insulating Body 120, some current will flow between the Measurement Electrodes 115 on the surface of Electrically Insulating Body 120 along the Opening 125. As a result, the electrical stability values obtained for a fluid sample will be biased unless the Electrode Arrangement 140 is frequently and thoroughly cleaned and the effect of this leakage current is otherwise minimized.

Turning to FIG. 2, the details of one embodiment of an Improved Electrode Arrangement for an Electrical Stability Tester (EST) according to the present invention, designated generally by reference numeral 200, will now be described. The improved Electrode Arrangement 200 includes a First Electrode 205 and a Second Electrode 210 precisely spaced apart and molded into an Electrically Insulating Body 220 with a round Opening 225 at one end. As would be appreciated by those of ordinary skill in the art, with the benefit of this disclosure, other methods may be used to install the electrodes in the insulating body. For instance, in one exemplary embodiment, the electrodes may be bonded or brazed into the insulating body. Preferably, the two electrodes are coaxial Nickel electrodes. In certain preferred embodiments, the Electrically Insulating Body 220 is made of ceramic because of ceramic's hardness, dimensional stability, chemical inertness, and its electrical insulation properties. The First Electrode 205 and the Second Electrode 210 are collectively referred to as Measurement Electrodes 215. The First Electrode 205 and the Second Electrode 210 are coupled to a power supply through a First Terminal 255 and a Second Terminal 245 respectively. As would be appreciated by those of ordinary skill in the art with the benefit of this disclosure, the terminal connections may be arranged in a variety of ways.

In order to distinguish between the two Measurement Electrodes 215, one will be referred to as the Reference Electrode 205 and the other as the Second Electrode 210. As would be appreciated by those of ordinary skill in the art, each of the two electrodes can be the reference electrode and this notation is only used for illustrative purposes. A Guard Electrode 230 is placed on the surface of the Electrically Insulating Body 220 so as to intercept any current flow paths between the Reference Electrode 205 and the Second Electrode 210, other than the paths that go through the fluid sample. In certain embodiments, the Guard Electrode 230 is positioned so that it faces the Electrode Gap 235. As would be appreciated by those of ordinary skill in the art, the Guard Electrode 230 can be formed in a variety of ways including, but not limited to, an electrically conductive coating on the surface of the Electrically Insulating Body 220 or a conductive part that is fastened or bonded in place. The Guard Electrode 230 is coupled to an electronic circuit through a Third Terminal 250. In an exemplary embodiment the electronic circuit maintains the Guard Electrode 230 at a potential substantially equal to the potential of the Reference Electrode 205. As those of ordinary skill in the art would appreciate, a number of different electronic circuitries can be used to keep the potential difference between the Guard Electrode 230 and the Reference Electrode 205 at or near zero.

Because the potential difference between the Guard Electrode 230 and the Reference Electrode 205 is maintained at or near zero, no current can flow between these two electrodes. As a result, any parasitic current trying to bypass the fluid sample (not shown) in the Electrode Gap 235 and flow between the Reference Electrode 205 and the Second Electrode 210 through the contaminants forming the Leakage Path 240 on the surface of the Electrically Insulating Body 220 will now be intercepted by the Guard Electrode 230.

In one embodiment of the present invention the level of contamination of the surface of the Electrically Insulating Body 220 along the Leakage Path 240 is measured and used to notify the operator if the Electrically Insulating Body 220 needs to be cleaned. The amount of current drawn from or supplied to the Guard Electrode 230 in order to maintain the potential at the Guard Electrode 230 substantially equal to that of the Reference Electrode 205 is substantially equal to the parasitic current intercepted by the Guard Electrode 230. As a result, the parasitic current and the current flowing through the fluid sample across the Measurement Electrodes 215 can be separately measured. The amount of parasitic current flowing on the surface of the Electrically Insulating Body 220 through the Leakage Path 240 is proportional to the amount of conductive contamination on the surface of the Electrically Insulating Body 220. Therefore, the measurement of the parasitic current flow will indicate the level of conductive contamination on the Electrically Insulating Body 220. As appreciated by those of ordinary skill in the art, various methods can be used to notify the operator of any contamination on the surface of the Electrically Insulating Body 220. In an exemplary embodiment, if the parasitic current exceeds a preset threshold, an indicator can be shown to alert the operator of the need for cleaning or maintenance.

Turning to FIG. 3, the details of another embodiment of an improved Electrical Stability Tester (EST) according to the present invention, designated generally by reference numeral 300, will now be described. The improved EST comprises a Cell Casing 302 which includes the various components of an EST sensor. In an exemplary embodiment the Cell Casing 302 is placed in an enclosure (not shown) and purged with air so that it can be mounted in a hazardous environment. In one embodiment, the Cell Casing 302 comprises a Top Part 304 and a Bottom Part 306. The joint between the Top Part 304 and the Bottom Part 306 is sealed. As would be appreciated by those of ordinary skill in the art with the benefit of this disclosure the Top Part 304 and Bottom Part 306 may be sealed using a variety of components. In one embodiment, an O-ring 308 is used to seal the Top Part 304 and the Bottom Part 306. In one embodiment, the Cell Casing 302 further includes at least one cavity which contains a Heating Element 312. In an exemplary embodiment three cavities (not shown) are created on the Cell Casing 302, each containing a Heating Element 312. As would be appreciated by those skilled in the art, a variety of different heating elements can be used. In one embodiment, the Heating Elements 312 are electric cartridge heaters. The Heating Elements 312 help keep the Cell Casing 302 and the fluid sample at a predetermined temperature during measurements in order to maintain the stability of the testing temperature. As would be appreciated by those of ordinary skill in the art, with the benefit of this disclosure, the heating can be accomplished by other means, including, but not limited to, heating elements mounted on the surface or placing the apparatus in an oven.

In certain preferred embodiments, the Cell Casing 302 is made with thermally conductive material to allow for easy transfer of heat through out the Cell Casing 302 and to the fluid sample in the Electrode Gap 235. Although a number of different thermally conductive materials can be used, in an exemplary embodiment, the Cell Casing 302 is made of stainless steel. Temperature Sensors 314 and 318 are used to monitor the temperature changes in the Cell Casing 302 and the fluid sample and are connected to the casing through the Connectors 334. In one embodiment, a first Temperature Sensor 314 is inserted in a temperature sensor cavity (not shown) in the Bottom Part 306 of the Cell Casing 302 through a first Connector 334. Similarly, a second Temperature Sensor 318 is inserted through the Top Part 304 of the Cell Casing 302 into the internal cavity of the Cell Casing 302 which contains the fluid sample. As such, the Temperature Sensors 314 and 318 can be used to monitor the temperature of the Cell Casing 302 and the fluid sample. As would be appreciated by those of ordinary skill in the art, with the benefit of this disclosure, a Thermal Switch 342 which is thermally conductively mounted on the Cell Casing 302 can detect and limit the impact of overheating of the Cell Casing 302. In an exemplary embodiment the thermal switch will interrupt the power supply to the Heating Elements 312 when it detects an overheating of the Cell Casing 302 or the fluid sample.

Attached to the Cell Casing 302 is an Improved Electrode Arrangement 200 for an Electrical Stability Tester in accordance with an embodiment of the present invention. The Improved Electrode Arrangement 200 is depicted in FIG. 2 and discussed above in detail.

In one embodiment, the Electrode Arrangement 200 is inserted into the Cell Casing 302 through a Hole 338 in the Cell Casing 302. A Matching Hole 340 in the Bottom Part 306 of the Cell Casing 302 allows the insertion of the Electrode Arrangement 200 so as to align the Electrode Gap 235 with the cavity formed between the Top Part 304 and the Bottom Part 306 of the Cell Casing 302. The Electrode Arrangement 200 is then sealed to the Cell Casing 302. In one embodiment, O-rings 326 are used to seal the Electrode Arrangement 200 to the Cell Casing 302. As would be appreciated by those of ordinary skill in the art with the benefit of this disclosure, different means can be used to hold the Electrode Arrangement 200 in place or adjust the position of the Electrode Gap 235 relative to the Cell Casing 302. In an exemplary embodiment the Electrode Arrangement 200 is held stationary in place by means of a Spring Clip 322 and the position of the Electrode Gap 235 with respect to the Cell Casing 302 can be precisely adjusted using a Set Screw 324 which acts as a position stop.

Figure 4:
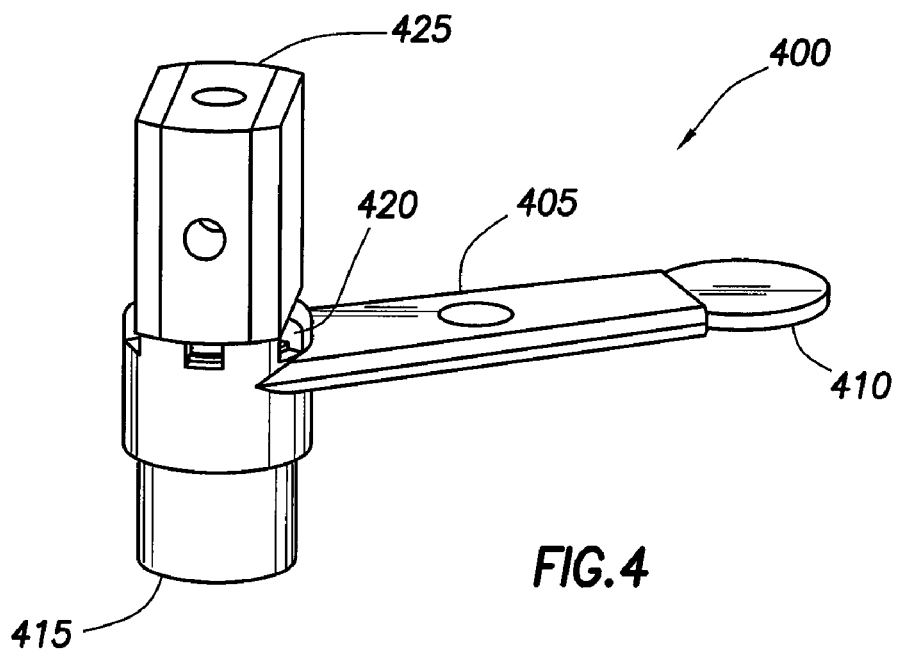
FIG. 4 is a side view of a Self Cleaning Mechanism in accordance with one embodiment of the present invention.

In certain embodiments the Cell Casing 302 includes a Self Cleaning Mechanism 400 which is depicted in detail in FIG. 4. In certain preferred exemplary embodiments the Self Cleaning Mechanism 400 comprises a rotationally mounted Arm 405 with a Vane 410 connected at one end. In one embodiment the Arm 405 is mounted on the end of a cantilevered Cross-Spring Pivot 415. The Cross-Spring Pivot 415 is a flexture bearing and has no sliding or rolling contact or close clearances and can be immersed directly into an abrasive fluid sample. Mounted as such, the Arm 405 has a limited range of rotation. In one embodiment, the range of rotation of the Arm 405 is between +/−15 degrees. Hence, the cleaning of the Electrode Gap 235 is accomplished by oscillating the rotational Arm 405 so that the Vane 410 on the end of the Arm 405 passes into the Electrode Gap 235 and back out. The Vane 410 is kept out of the Electrode Gap 235 when taking the electrical stability measurements. In an exemplary embodiment, the Vane 410 is made of an abrasive resistant material so that it maintains its close fit in the Electrode Gap 235. In one embodiment there is a Flow Passage 420 in the Arm 405. This Flow Passage 420 allows the fluid sample to circulate through the center of the Cross-Spring Pivot 415 to flush out solids that may collect there.

In certain embodiments the oscillation of the Vane 410 is accomplished through interaction with the magnetic field of a Magnetic Armature 425 which is mounted co-axially with the Cross-Spring Pivot 415 and the Rotational Arm 405. In one embodiment the Magnetic Armature 425 is fitted closely into the cavity of a thin walled Boss 328 that protrudes from the Top Part 304 of the Cell Casing 302. A pair of opposed Cores 330 forming a magnetic path are positioned on the external wall of the Boss 328. The Cores 330 are coupled to the inside of a Coil 332. When current flows through the wire (not shown) wrapped around the Coil 332 a magnetic flux is induced in the Cores 330. The induced magnetic flux interacts with the magnetic field of the Magnetic Armature 425 thereby controlling the rotation of the Arm 405 and the position of the Vane 410. As would be appreciated by those of ordinary skill in the art with the benefit of this disclosure other methods can be used to accomplish the oscillation of the Rotational Arm 405. For instance, in another exemplary embodiment a shaft may be extended through a seal in the Top Part 304 or the Bottom Part 306 and an external torque motor or air cylinder may be used to activate the arm. In certain embodiments an inductive or capacitive proximity sensor (not shown) may be used to detect malfunctions and provide motion feed back to a controller (not shown).

In some exemplary embodiments the Vane 410 is made of an insulating material. In order to determine if the Electrode Arrangement 200 is clean enough, the Vane 410 is placed in the Electrode Gap 235 and then an electrical stability measurement is obtained. Because the Vane 410 is made of insulating material, any current flowing between the Measurement Electrodes 215 must flow through any contaminants on the surface of the Electrically Insulating Body 220. If the Electrode Arrangement 200 is clean, the voltage obtained in the electrical stability measurement must be substantially equal to the maximum voltage that can be reached by the instrument.

As would be appreciated by those of ordinary skill in the art, with the benefit of this disclosure, the self cleaning mechanism is not limited to the arm and vane structure disclosed above and may comprise other devices. In one embodiment, the self cleaning mechanism may comprise a disk with a circular hole in its center. The size of the hole is adjusted to correspond to the size of the surface of the Measurement Electrodes 215. The Electrode Gap 235 is cleaned by automatically oscillating or rotating the disk in the Electrode Gap 235. However, when an electrical stability measurement is to be taken by the Electrode Arrangement 200 the disk is moved such that the circular hole in the disk is aligned with the surface of the Measurement Electrodes 215. At this position the fluid sample and not the disk is located in the Electrode Gap 235.

In certain embodiments, the flow of the fluid sample into the Electrode Gap 235 in the Cell Casing 302 is controlled using valves and pumps (not shown) and the fluid sample is screened to trap particles that could interfere with the electrical stability measurement. As would be appreciated by those of ordinary skill in the art with the benefit of this disclosure, the fluid sample can be introduced into and removed from the Cell Casing 302 in a variety of ways. In one embodiment, the fluid sample flows into and out of the Cell Casing 302 through two Hose Connectors 336. In an exemplary embodiment, the direction of flow of the fluid sample may be periodically reversed to aid in preventing the build up of solid particles in the system. In one embodiment once the fluid sample enters the Cell Casing 302 it substantially fills the cavity between the Top Part 304 and the Bottom Part 306 of the Cell Casing 302 as well as the Electrode Gap 235. Furthermore, in an exemplary embodiment, the cavity in the Cell Casing 302 is designed so as to direct a fluid sample flow through the Electrode Gap 235, around the Vane 410 assembly, and through the Cross-Spring Pivot 415 with minimum clearance, thereby minimizing the total volume of fluid sample required for obtaining an electrical stability measurement.

Figure 5:
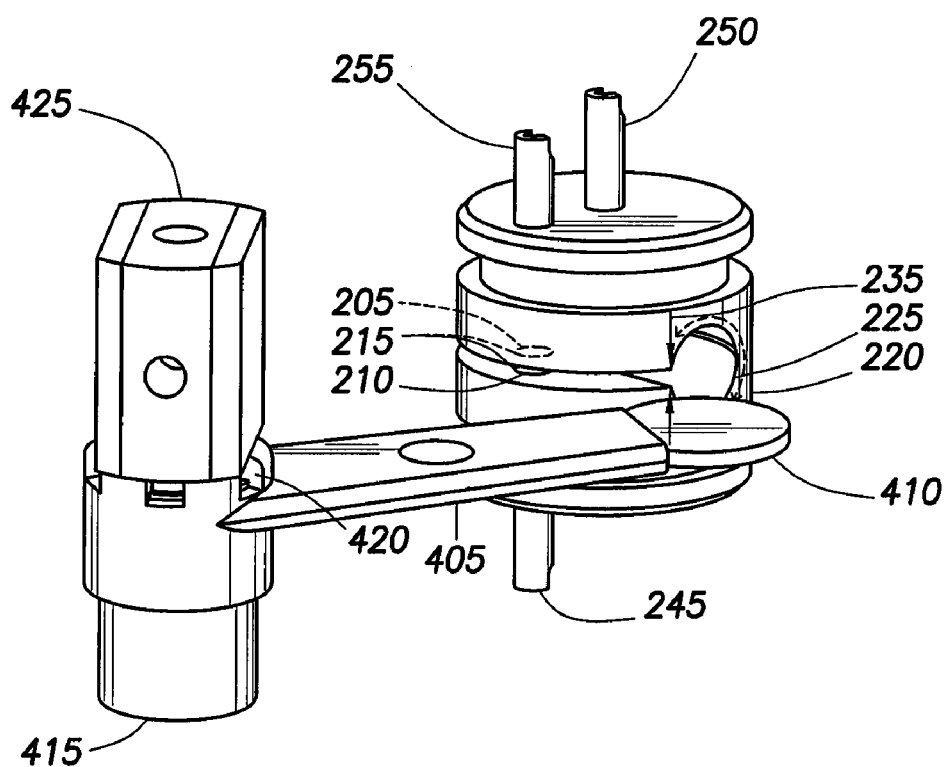
FIG. 5 is a side view of a Self Cleaning Electrical Stability Tester Cell with the vane of the Self Cleaning Mechanism outside the electrode gap.
Figure 6:
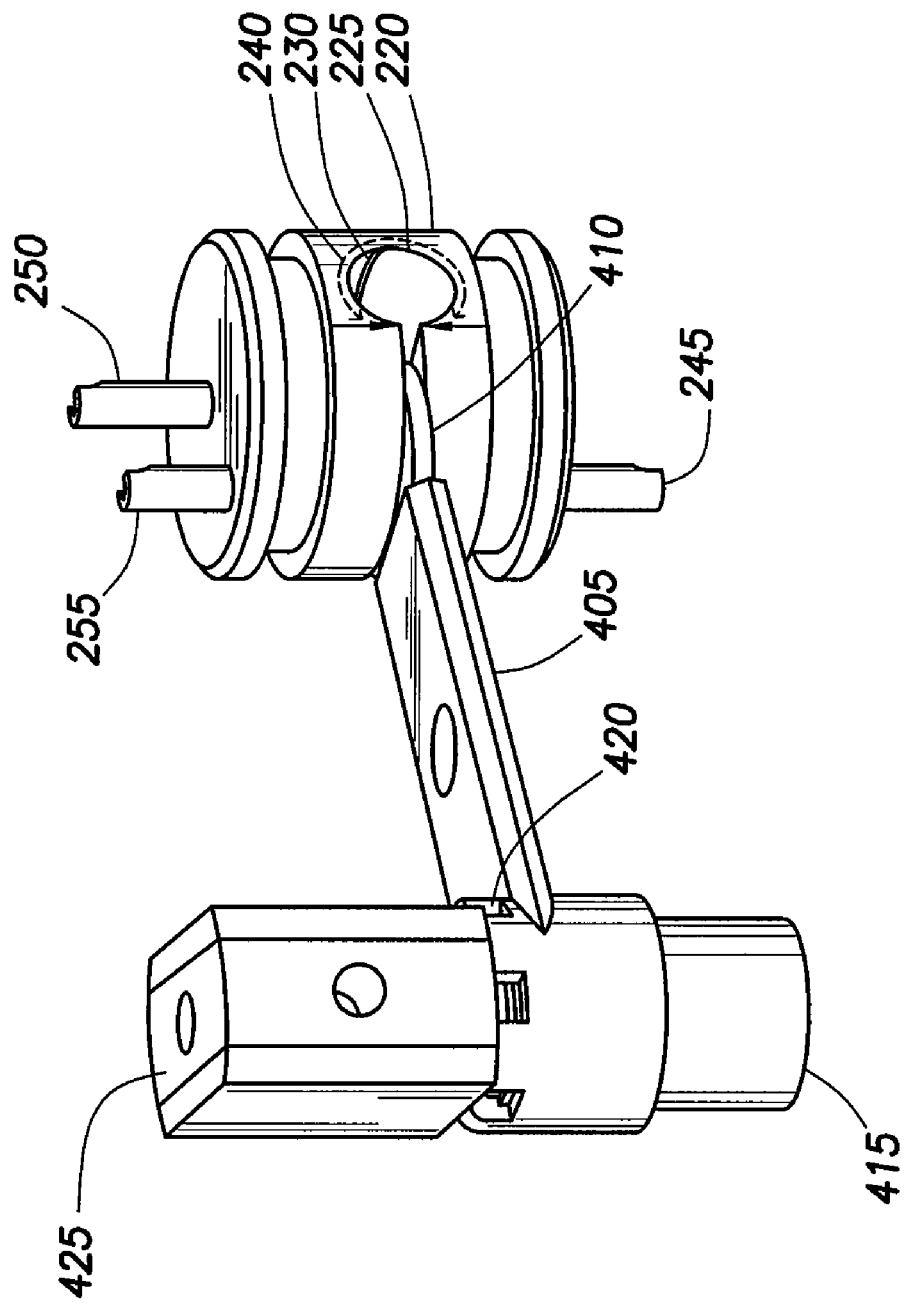
FIG. 6 is a side view of a Self Cleaning Electrical Stability Tester Cell with the vane of the Self Cleaning Mechanism going in to the electrode gap.

Shown in FIGS. 5 and 6 is the arm and vane self cleaning mechanism at the extremes of its motion. Depicted in FIG. 5 is a side view of a Self Cleaning Electrical Stability Tester Cell with the Rotational Arm 405 positioned so that the Vane 410 is outside the Electrode Gap 235. FIG. 6 shows a side view of the Self Cleaning Electrical Stability Tester Cell with the Rotational Arm 405 as the Vane 410 is being inserted into the Electrode Gap 235.

As would be appreciated by those of ordinary skill in the art, with the benefit of this disclosure, the improved electrode arrangement of the present invention may be adapted for use with the probes currently used in Electrical Stability Testers, such as for example the Fann 23D, in order to improve their performance.

Therefore, the present invention is well-adapted to carry out the objects and attain the ends and advantages mentioned as well as those which are inherent therein. While the invention has been depicted and described by reference to exemplary embodiments of the invention, such a reference does not imply a limitation on the invention, and no such limitation is to be inferred. The invention is capable of considerable modification, alternation, and equivalents in form and function, as will occur to those ordinarily skilled in the pertinent arts and having the benefit of this disclosure. The depicted and described embodiments of the invention are exemplary only, and are not exhaustive of the scope of the invention. Consequently, the invention is intended to be limited only by the spirit and scope of the appended claims, giving full cognizance to equivalents in all respects. The terms in the claims have their plain, ordinary meaning unless otherwise explicitly and clearly defined by the patentee.

What is claimed is:

1. A fluid stability measurement device comprising:
an insulating body;
an electrode gap cleaning device coupled to the insulating body;
a reference electrode coupled to the insulating body having a first electrical potential;
a second electrode coupled to the insulating body having a second electrical potential; and
a guard electrode on a surface of the insulating body,
wherein a gap is formed between a surface of the reference electrode and a surface of the second electrode, and
wherein the guard electrode is located in a surface path on the insulating body between the reference electrode and the second electrode.

2. The device of claim 1, wherein the guard electrode has an electrical potential substantially equal to the first electrical potential.

3. The device of claim 1, further comprising a current measurement device, wherein the current measurement device measures a current flow between the reference electrode and the second electrode.

4. The device of claim 1, further comprising a potential difference measurement device, wherein the potential difference measurement device measures a potential difference between the reference electrode and the second electrode.

5. The device of claim 1, wherein the fluid is a drilling fluid.

6. The apparatus of claim 1, wherein the electrode gap cleaning device comprises:
an arm rotatable through a plane lying in the electrode gap; and
a vane coupled to the arm,
wherein the arm oscillates the vane in and out of the gap between the reference electrode and the second electrode.

7. The apparatus of claim 1, wherein the electrode gap cleaning device comprises one of an oscillating disk, a rotating disk, or a brush.

8. The apparatus of claim 1, wherein the insulating body comprises one of ceramic or plastic.

9. A method of determining electrical stability of a fluid comprising:
placing the fluid in a gap between a reference electrode having a first potential and a second electrode having a second potential;
coupling the reference electrode and the second electrode with an insulating material;
intercepting a path on the insulating material between the reference electrode and the second electrode with a guard electrode;
increasing a potential difference between the reference electrode and the second electrode;
measuring an amount of current flow between the reference electrode and the second electrode; and
measuring an amount of current flow between the reference electrode and the guard electrode and producing an indication if the amount of current flow is more than a threshold value.

10. The method of claim 9, further comprising measuring a potential difference between the reference electrode and the second electrode.

11. The method of claim 9, wherein the guard electrode is at a potential substantially equal to the first potential.

12. The method of claim 9, wherein the increase in potential difference between the reference electrode and the second electrode is accomplished by increasing an AC voltage applied between the reference electrode and the second electrode.

13. The method of claim 9, wherein the fluid is passed through a filter before entering the gap between the reference electrode and the second electrode.

* * * * *